United States Patent [19]

Ishiwatari

[11] Patent Number: 5,972,983

[45] Date of Patent: Oct. 26, 1999

[54] PEST REPELLENT

[75] Inventor: Takao Ishiwatari, Toyonaka, Japan

[73] Assignee: Sumitomo Chemical Company Limited, Osaka, Japan

[21] Appl. No.: 09/179,690

[22] Filed: Oct. 27, 1998

[30] Foreign Application Priority Data

Dec. 5, 1997 [JP] Japan ..... 9-335403

[51] Int. Cl.$^6$ ..... A01N 25/00; A01N 25/32; A01N 25/24; A01N 25/08
[52] U.S. Cl. ..... 514/389; 514/919; 424/403; 424/405; 424/409; 424/410; 424/411; 424/412; 424/413; 424/414; 424/416
[58] Field of Search ..... 514/389, 919; 424/403, 405, 409, 410, 411, 412, 413, 414, 416

[56] References Cited

U.S. PATENT DOCUMENTS

| 4,176,189 | 11/1979 | Itaya et al. | 514/389 |
| 5,595,747 | 1/1997 | Kuroda et al. | 424/405 |
| 5,653,990 | 8/1997 | Iwasaki et al. | 424/405 |

FOREIGN PATENT DOCUMENTS 0823213  2/1998  European Pat. Off. .

*Primary Examiner*—Frederick Krass
*Attorney, Agent, or Firm*—Stevens, Davis, Miller & Mosher, L.L.P.

[57] ABSTRACT

A pest repellent comprising improthrin as an active ingredient and inert carrier has excellent effect for repelling arthropod, mollusca and annelida. It is especially useful for repelling cockroaches.

3 Claims, No Drawings

PEST REPELLENT

FIELD OF THE INVENTION

The present invention relates to pest repellents and methods for repelling pests, especially suitable for repelling cockroaches.

BACKGROUND OF THE INVENTION

Pests such as cockroaches transmit diseases. The presence of these pests in environments wherein humans inhabit increase the chances to be exposed to diseases. Efficacious agents and methods which control pests from inhabiting the human environment have been desired. Since pests can adapt to exposure, it would be an advantage if a multiplicity of methods and agents are available for controlling these pests.

Aerosol compositions comprising of N,N-diethyl-m-toluamide have been utilized to repel mosquitoes and black flies. However, N,N-diethyl-m-toluamide may be insufficient as a pest repellent. The deficiency of sustaining any repelling activity after a long period of time has deemed N,N-diethyl-m-toluamide as an unpalatable candidate for a pest repellent. In addition, the efficacy of N,N-diethyl-m-toluamide is insufficient when certain pests such as cockroaches are targeted.

Japanese Laid-open patent No. sho56-92803-A discloses ester compounds such as empenthrin as an active ingredient of a cockroach repellent. These ester compounds may have the ability to repel pests for a given period, but also greatly decrease efficacy after a long period of time.

It is tedious to continually dispose an agent to repel pests. Therefore, it would be of advantage if a pest repellent can efficaciously repel pests for a long period of time with one disposal. It would also be of advantage if a pest repellent were developed to target a larger variety of pests and include pests which have been difficult to repel such as the cockroach.

SUMMARY OF THE INVENTION

The present invention sets forth a pest repellent that employs imiprothrin [2,4-dioxo-1-(2-propenyl) imidazolazin-3-ylmethyl (1R)-cis, trans-chrysanthemate], and a pest repelling method that utilizes imiprothrin.

DETAILED DESCRIPTION OF THE INVENTION

Imiprothrin may be produced by following U.S. Pat. No. 4,176,189.

The pest repellent of the present invention may be the active ingredient of imiprothrin itself, but providing imiprothrin as a formulation is generally standard. More specifically, a formulation wherein imiprothrin is supported on an appropriate carrier is standard. Sheet formulations, formulations wherein imiprothrin is kneaded into a resin, emulsifiable concentrates, oil formulations, wettable powders, flowable formulations, granules, dusts, enmicrocapsulated formulations, aerosols, heat volatile formulations, and so on are examples of possible formulations.

The sheet materials are not especially restricted when the pest repellent is formulated as a sheet. Papers, synthetic resins, cloths, and so on are set forth as examples of the said sheet materials. The formulated sheet may generally comprise about 0.01 to 10 g of imiprothrin for every 1 $m^2$ of the said sheet.

Furthermore, in the event the pest repellent takes the formulation of emulsifiable concentrates or oil formulation, the said formulations generally comprise about 0.01 to 10% by weight of imiprothrin.

In addition to imiprothrin, any other pest repelling ingredient may be incorporated to the pest repellent. Examples of the other pest repelling ingredients that may be additionally incorporated are N,N-diethyl-m-toluamide, carane-3,4-diol, 1-methylpropyl 2-(2-hydroxyethyl)-1-piperizinecarboxylate, p-menthane-3,8-diol, pest repelling plant essential oils and so on.

The pest repellent is generally utilized by disposing the pest repellent at the targeted area of pest repelling. The typical household, warehouse, dining areas, and so on areas wherein the pest may invade are examples of objective areas wherein the pest repellent generally may be disposed. It is especially effective to repel pests such as cockroaches by setting the sheet formulation of the pest repellent under intricate machinery such as a personal computer, copy machine, and telephone, or under vending machines, or so on. The pest repellent may also be utilized to repel pests such as mosquitoes (Culicidae), black flies (Simuliidae), stable flies (Stomoxyidae) by disposing onto the body or clothes when the pest repellent is formulated as an ethanol solution, isopropanol solution, lotion or cream formulation, or so on. The pest repellent may further be utilized to repel or stop the invasion of pests such as ants, pill bugs, sow bugs, millipedes (Anamorpha), millipedes (Epimorpha), centipedes, and so on by dispersing around the perimeter of a typical household, warehouse, dining areas, and so on.

When the pest repellent is formulated as emulsifiable concentrates, wettable powders, flowable formulations, enmicrocapsulated formulations, and so on, a water dilution is applied. When the pest repellent is formulated as granules, dusts, aerosols, oil formulations, or so on, the pest repellent is applied by itself. The amount of imiprothrin employed for the pest repellent does vary with the objective location, utilization method, variation of formulation, targeted pest, and so on, but usually is about 0.01 g to 10 g for 1 $m^2$.

The pest repellent of the present invention may be employed in various methods but, a method wherein the pest is exposed with the present invention either directly or by previously preparing the pest repellent in an area that is possible for the pest to be exposed to the pest repellent is preferable. More specifically, the pest repellent may be applied in a pest repelling method such as dispersal, spraying, spreading, placing, pasting, or so on. In addition, the pest repellent may also be employed in a pest repelling method wherein the pest repellent is supported on the ingredients of household items by means of incorporation such as spreading, soaking, kneading and mixing, dripping/dropping, and so on before the said ingredient is formed to an household item. The utilization of the household item that was formed from the said ingredients that preserve the pest repellent will repel pests and is also a method to repel pests.

The pest repellent is not limited to repel just Dictyoptera such as German cockroach (*Blattella germanica*), smoky-brown cockroach (*Periplaneta fuliginosa*), American cockroach (*Periplaneta americana*), brown cockroach (*Periplaneta brunnea*), oriental cockroach (*Blatta orientalis*), and so on; Lepidoptera such as casemaking clothes moth (*Tinea pellionella*), webbing clothes moth (*Tineola bisselliella*), Indian mean moth (*Plodia interpunctella*), and so on; Diptera such as Culex spp., Anopheles spp., Aedes spp., Muscidae, small fruit flies or vinegar flies (Drosophilidae), moth flies or sand flies (Psychodidae), Phoridae, and so on; Coleoptera such as the maize weevil (*Sitophilus zeamais*), adzuki bean weevil (*Callosobruchus chinensis*), black carpet beetle (*Attagenus unicolorjaponicus*), varied carpet beetle (*Authrenus verbasci*), Anobiidae, powderpost beetle (*Lyctus brunneus*), robe beetle (*Paederus fuscipes*), and so on; Hymenoptera such as ants (Formicidae), Bethylidae, and so on; Siphonaptera such as human flea (*Pulex irritans*), cat flea (*Ctenocephalides felis*), and so on; lice (Anoplura) such as body louse (*Pudiculus humanus*), crab louse (*Pthrius pubis*), and so on, Isoptera such as *Reticulitermes speratus,* Formosan subterranean termite (*Coptotermes formosanus*), and so on; and so on harmful insects, but is also efficacious in repelling mites and ticks (Acarina) such as house dust mites (for example, Acaridae, Dermanyssidae, Pyroglyphidae, Chetyletidae, and so on), ticks (for example, *Boophilus microplus*), Ornithonyssus spp., and so on; spiders; Scorpions (Scorpionida); Oniscoidea such as pillbugs and sow bugs; millipeds (Chilopoda) such as Anamorpha, Epimorpha, centipede, and so on; Gastropoda such as slugs and snails; leeches; and so on. Namely, the pests include arthropod, mollusca, annelida, and so on.

EXAMPLES

Example 1

A shelter was prepared by constructing an entrance/exit into a paper box (length 7 cm×width 10 cm×height 2 cm). A sheet formulation (7.6 cm×2.6 cm) was then prepared by spreading 0.4 ml of an acetone solution comprising of 0.25% by weight of imiprothrin onto a glass slide and then drying the formulation. The said sheet formulation was then located in a position on the floor in the said shelter wherein the said formulation follows the entrance/exit. Food, water, the obtained shelter containing the sheet formulation, and 10 male and female adult cockroaches were deposited into a plastic case (length 30 cm×width 20 cm×height 8 cm). The quantity of cockroaches in the said shelter was counted 24 hours later.

In addition, a shelter containing the sheet formulation was preserved for 2 weeks at 25° C. and wherein the humidity was at 60%. Food, water, the preserved shelter, and 10 male and female adult cockroaches were re-deposited into the emptied plastic case. The quantity of cockroaches in the said shelter was counted 24 hours later.

Furthermore, empenthrin and N,N-diethyl-m-toluamide (Deet) were similarly tested for the ability to repel German cockroaches from the shelter. A control was also performed by utilizing a shelter without repellent disposal.

The results are given in table 1. Within the table, a "−" represents that the invasion rate of cockroaches into the shelter was less than 30%, a "+" represents 30% or more to less than 50%, and a "++" represents 50% or more.

TABLE 1

|  | results right after disposal | results 2 weeks later |
|---|---|---|
| imiprothrin | − | − |
| empenthrin | + | ++ |
| Deet | − | ++ |
| No Compositional disposal | ++ | |

The insect repellent of the present invention is effective in repelling insects such as cockroaches. Imiprothrin was able to repel insects 2 weeks after disposal while other well known pest repellents such as empenthrin and N,N-diethyl-m-toluamine were ineffective after such an elapse of time. The ability of imiprothrin to sustain repelling activity after a long period of time negates the necessity to tediously continue pest repellent disposal to efficaciously repel pests. In addition, the ability of imiprothrin to repel a difficult pest such as the cockroach also deems imiprothrin as an excellent repellent against a variety of pest.

What is claimed is:

1. A pest repellent method, wherein a sheet formulation which comprises imiprothrin is applied to the locus where a pest inhabits or invades.

2. A pest repellent method according to claim 1, wherein the pest is a cockroach.

3. The pest repellent method according to claim 1 wherein the sheet formulation comprises 0.01 to 10 g of imiprothrin per 1 $m^2$ of sheet.

* * * * *